(12) United States Patent
Hameed et al.

(10) Patent No.: US 8,475,393 B1
(45) Date of Patent: Jul. 2, 2013

(54) METHODS AND DEVICES FOR OBTAINING BIOPSY SAMPLES

(75) Inventors: Salmaan Hameed, Palo Alto, CA (US); Adolph G. Valdez, Palo Alto, CA (US); Moshe Zilversmit, Palo Alto, CA (US)

(73) Assignee: Chest Innovations, Inc., Pleasanton, CA (US)

( * ) Notice: Subject to any disclaimer, the term of this patent is extended or adjusted under 35 U.S.C. 154(b) by 2 days.

(21) Appl. No.: 12/958,394

(22) Filed: Dec. 1, 2010

Related U.S. Application Data

(60) Provisional application No. 61/265,550, filed on Dec. 1, 2009.

(51) Int. Cl.
*A61B 10/00* (2006.01)

(52) U.S. Cl.
USPC .......................................... 600/564; 600/567

(58) Field of Classification Search
USPC ................................... 600/562–568; 604/542
See application file for complete search history.

(56) References Cited

U.S. PATENT DOCUMENTS

| 5,788,651 | A | * | 8/1998 | Weilandt | 600/567 |
| 6,626,890 | B2 | * | 9/2003 | Nguyen et al. | 604/542 |
| 2008/0281226 | A1 | * | 11/2008 | Peters | 600/567 |

* cited by examiner

*Primary Examiner* — Brian Szmal
*Assistant Examiner* — Megan Leedy
(74) *Attorney, Agent, or Firm* — Dorsey & Whitney LLP

(57) ABSTRACT

Methods and devices for obtaining biopsy samples are described. In one embodiment, a capture tube with capture arms slides over a core tube to grasp and/or cut a tissue sample. Forceps with jaws may be used to hold the tissue before the capture tube is used to obtain the tissue sample. In another embodiment, a core tube includes needle channels in which capture needles are advanced to grasp and/or penetrate a tissue sample. In yet another embodiment, a capture tube includes grasping arms which close through slots in a core tube to grasp and/or cut a tissue sample.

10 Claims, 13 Drawing Sheets

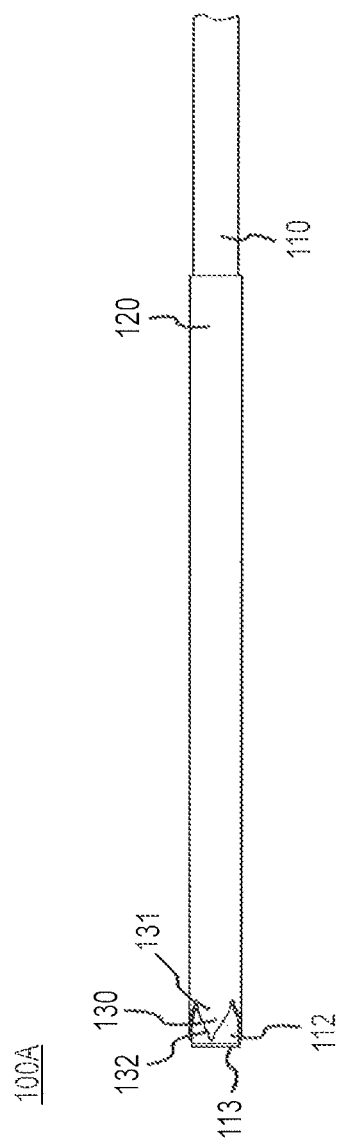
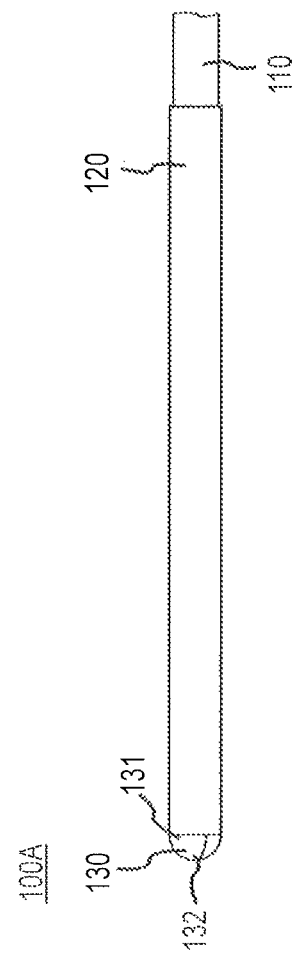
FIG. 1A
FIG. 1B

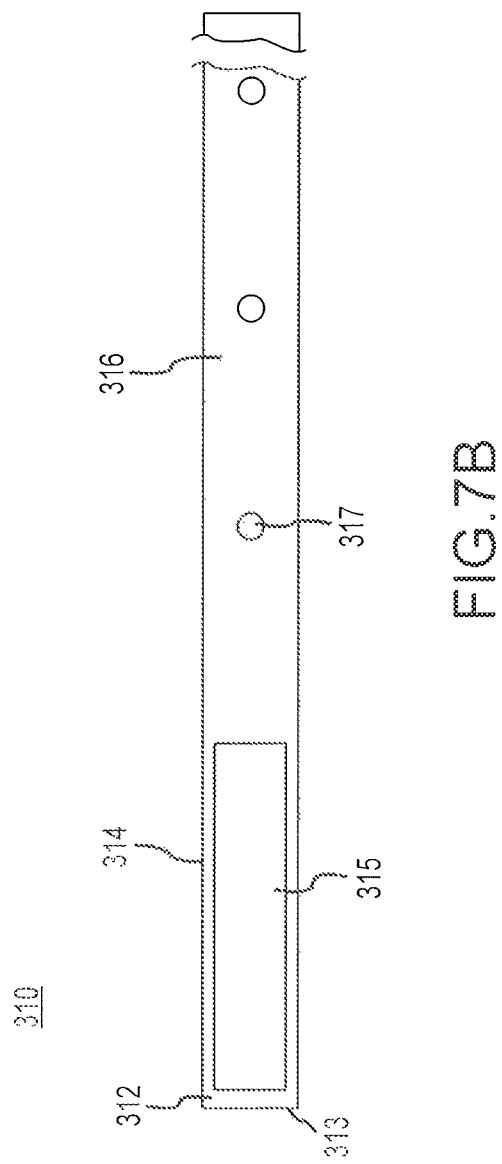

METHODS AND DEVICES FOR OBTAINING BIOPSY SAMPLES

CROSS-REFERENCE TO RELATED APPLICATIONS

This application claims the benefit of U.S. provisional application Ser. No. 61/265,550, filed Dec. 1, 2009.

BACKGROUND

Biopsy samples are used to assess tissue for various conditions. Biopsy samples may need to be obtained from a lung, kidney, liver, or other internal organ. Ideally, the biopsy sample is obtained with as little damage as possible to the tissue. Also, the biopsy sample is sufficient for meaningful analysis.

Tissue samples for lung and other biopsies may be performed using a wedge resection. A wedge resection removes a tissue sample having a size of approximately 2 cm by 3 cm. Cutting out a tissue sample of this size leaves a sizable wound that typically requires the insertion of a chest tube to prevent pneumothorax, a lengthy healing time, and additional procedures to address other complications. In addition, the size of the wounds typically cause considerable bleeding after the biopsy.

Tissue samples for lung and other biopsies may also be performed using needle biopsies, which present their own challenges. One of these challenges is to successful break off the sample in the needle. Another challenge is obtaining enough of the tissue for biopsy. The use of a larger needle in an effort to obtain more tissue may result in a larger wound at the biopsy site.

What is needed are methods and devices for obtaining enough of a biopsy sample, without having to use a wedge resection.

What is also needed are methods and devices for obtaining a biopsy sample that reduce the size of the wound and reduce the amount of bleeding at the biopsy site.

SUMMARY

A biopsy device for obtaining a biopsy sample from a tissue is described. The biopsy device comprises a core tube and a capture tube. The core tube includes a leading section including a leading edge. The core tube also includes a slotted section proximal to the leading section. The slotted section includes a slot formed longitudinally in a wall of the core tube. The core tube also an inner cooling section proximal to the slotted section. The inner cooling section includes a plurality of inner cooling holes formed in the wall of the core tube.

The capture tube is slidably and rotatably coupled substantially concentrically around the core tube. The capture tube includes a distal section. The capture tube also includes a capture section proximal to the distal section. The capture section includes a capture arm formed longitudinally in a wall of the capture tube. The capture arm is biased inward. The capture arm is prevented from moving inward when not aligned with the slot in the core tube. The capture arm is allowed to move inward when aligned with the slot in the core tube. The capture tube also includes an outer cooling section proximal to the capture section. The outer cooling section includes a plurality of outer cooling holes formed in the wall of the capture tube. The inner cooling holes are capable of being aligned with the outer cooling holes.

BRIEF DESCRIPTION OF DRAWINGS

FIGS. 1A-1B show one embodiment of a biopsy device 100A.

FIGS. 7A-7D show yet another embodiment of a biopsy device 300.

DETAILED DESCRIPTION

Figure 2A:
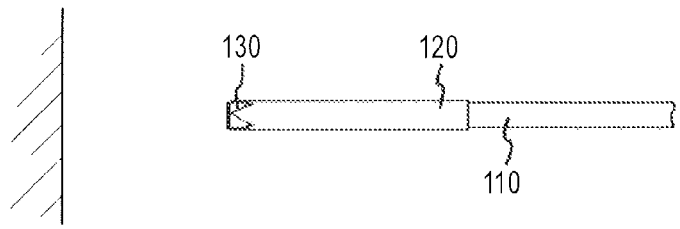
FIGS. 2A-2D show one method of using biopsy device 100A.

FIGS. 1A-1B show one embodiment of a biopsy device 100A. FIG. 1A shows biopsy device 100A in an open position. FIG. 1B shows biopsy device 100B in a closed position.

Biopsy device 100A includes a core tube 110 and a capture tube 120 with capture arms 130.

Core tube 110 includes a distal end 112 with a leading edge 113 configured to cut tissue. Leading edge 113 is configured to work with an RF or other energy source for cutting tissue. Leading edge 113 may be blunt or atraumatic. Alternatively, leading edge 113 may be sharp, serrated, or other suitable configuration.

Capture tube 120 is positioned concentrically around core tube 110. Capture tube 120 has an inside diameter that is greater than and outside diameter of core tube 110. Capture tube 120 can slide and rotate around core tube 110.

One or more capture arms 130 are coupled to a distal end 122 of capture tube 120. Capture arms 130 are biased inward toward the center of capture tube 120. Capture arms 130 have proximal ends 131 that are attached to distal end 122 of capture tube 120. Capture arms 130 have distal ends 132 that are free. Capture arms 130 may be blunt and coupled to an RF or other energy source to aid in cutting tissue. Alternatively, capture arms 130 may be sharp. Capture arms 130 may be substantially triangular or other suitable shape.

Capture tube 120 may be pulled back with respect to core tube 110 so that capture arms 130 are proximal to distal end 112 of core tube 110. In this open configuration, core tube 110 holds open capture arms 130. Capture tube 120 may also be advanced with respect to core tube so that capture arms 130 are distal to distal end 112 of core tube 110. In this closed configuration, capture arms 130 are allowed to close toward the center of capture tube 120. In the embodiment shown, four capture arms 130 close into a domed or hemisphere-like shape.

FIGS. 2A-2D show one method of using biopsy device 100A. Biopsy device 100A may be introduced through a previously placed sheath or cannula to reach the target tissue.

FIG. 2A shows biopsy device 100A in a cutting configuration. Capture tube 120 is pulled back with respect to core tube 110 so that capture arms 130 are proximal to distal end 112 of core tube 110. Core tube 110 holds open capture arms 130.

Figure 2B:
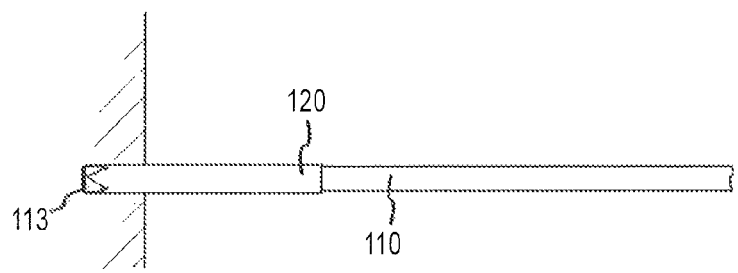

FIG. 2B shows biopsy device 100A advanced into a tissue. Core tube 110 is advanced into the tissue by using leading edge 113 and an RF energy source to cut into the tissue to a desired depth. The use of an RF energy source reduces bleeding.

Figure 2C:
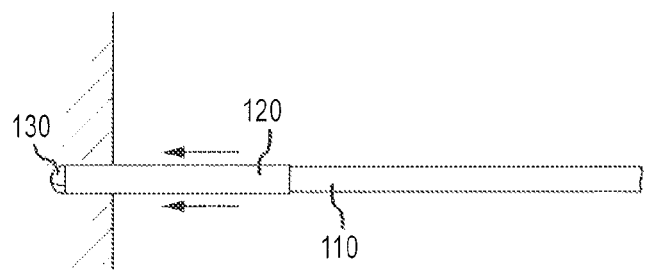

FIG. 2C shows biopsy device 100A in a capture configuration. Capture tube 120 is advanced with respect to core tube 110. Capture arms 130 close inward toward the center of capture tube 120 to capture the sample. Capture arms 130 may be coupled to an RF energy source to aid in cutting the tissue.

Figure 2D:
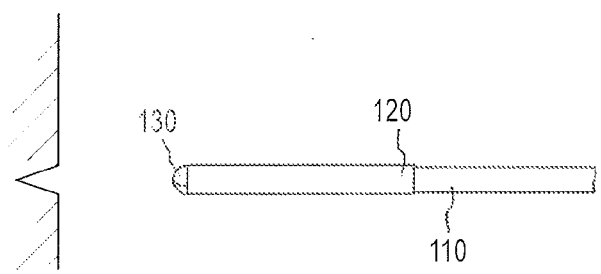
Figure 3A:
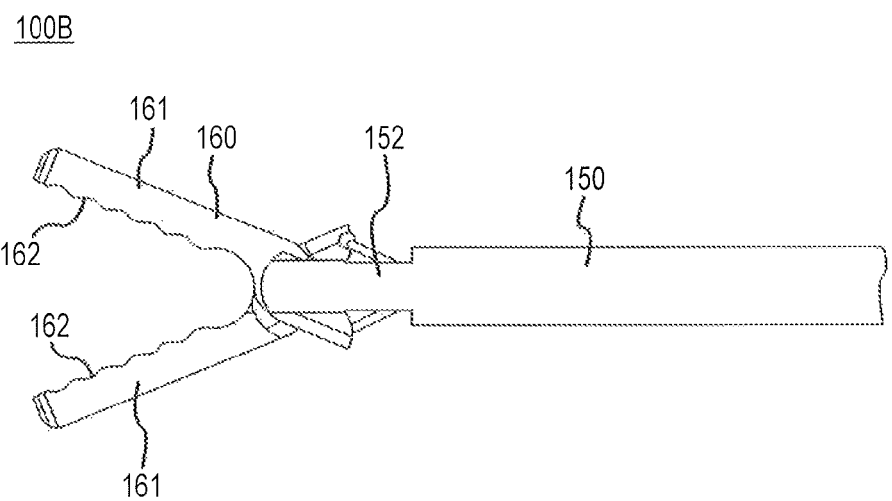
FIGS. 3A-3D show another embodiment of a biopsy device 100B.
Figure 3B:
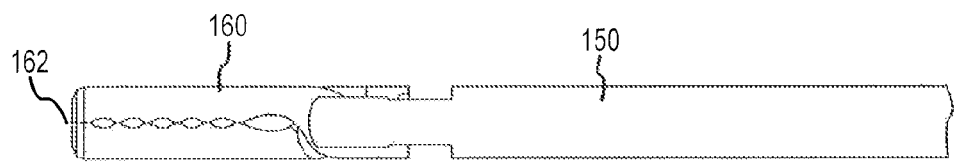
Figure 3C:
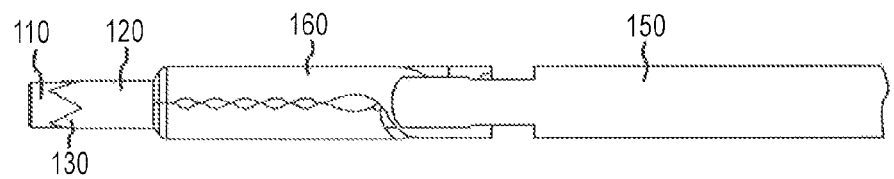
Figure 3D:

FIG. 2D shows biopsy device 100A withdrawn from the tissue. Leading edge 113 may be used with an RF energy source to coagulate the tissue to reduce bleeding. Core tube 110 contains the sample, which may be detached from the tissue with cutting, RF energy, and/or pulling. Capture tube 120 may be pulled back to open capture arms 130 and allow the sample to be removed from core tube 110.

FIGS. 3A-3D show another embodiment of a biopsy device 100B.

Biopsy device 100B is similar to biopsy device 100A, but also includes a forceps catheter 150 with forceps 160.

Forceps catheter 150 is concentrically positioned around capture tube 120. Forceps catheter 150 includes a central channel 151 in which capture tube 120 can slide and rotate. Forceps catheter 150 includes a distal end 152 with forceps 160. Forceps 160 includes jaws 161 that are configured to grasp and/or penetrate tissue. Jaws 161 may have teeth 162 that are sharp, blunt, jagged, wavy, or other suitable configuration. When closed, jaws 161 form an opening 162 through which capture tube 120 can pass.

FIGS. 4A-4D show one method of using biopsy device 100B. Biopsy device 100B is used in a manner similar to biopsy device 100A, with forceps 160 being used to first grasp and hold tissue.

Figure 4A:
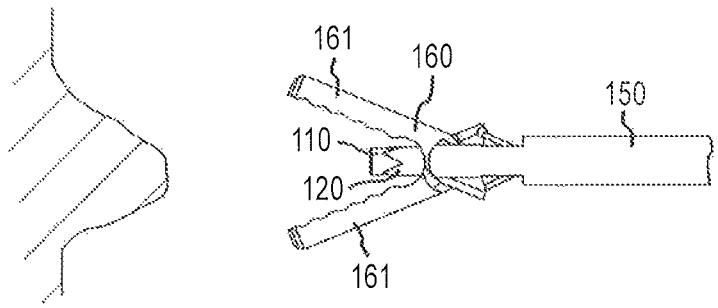
FIGS. 4A-4D show one method of using biopsy device 100B.

FIG. 4A shows biopsy device 100B in a grasping configuration. Jaws 161 of forceps 160 are open and may be used to grasp and/or penetrate a target tissue. Core tube 110 and capture tube 120 are at least partially retracted inside central channel 151 of forceps catheter 150. Capture tube 120 is pulled back with respect to core tube 110. Core tube 110 holds open capture arms 130.

Figure 4B:
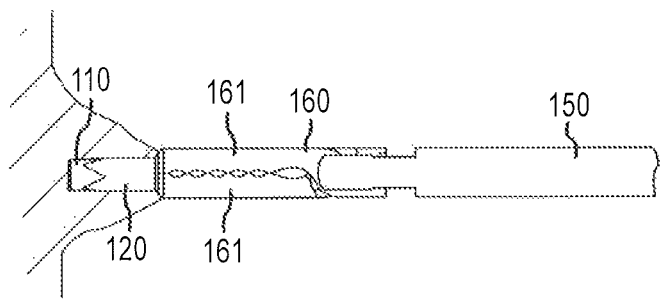

FIG. 4B shows biopsy device 100B advanced into a tissue. Jaws 161 of forceps 160 are closed. Core tube 110 and capture tube 120 are extended outside forceps 160 through opening 162. Core tube 110 is advanced into the tissue by using leading edge 113 and an RF energy source to cut into the tissue to a desired depth. The use of an RF energy source reduces bleeding.

Figure 4C:
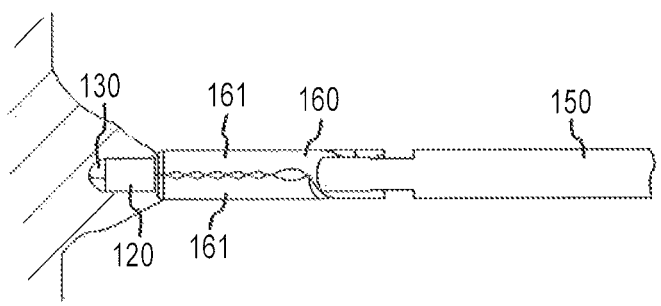

FIG. 4C shows biopsy device 100B in a capture configuration. Capture tube 120 is advanced with respect to core tube 110. Capture arms 130 close inward toward the center of capture tube 120 to capture the sample. Capture arms 130 may be coupled to an RF energy source to aid in cutting the tissue.

Figure 4D:
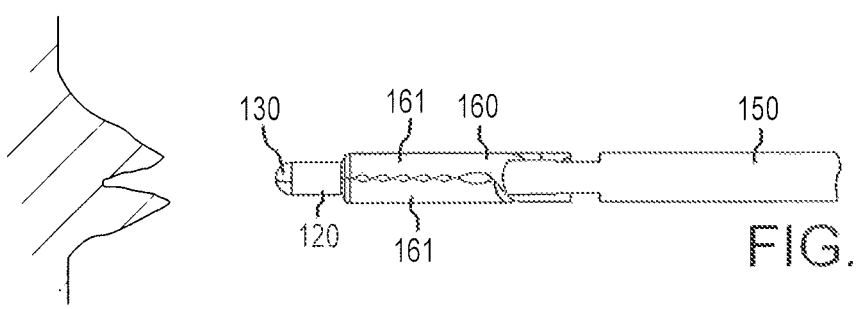

FIG. 4D shows biopsy device 100B withdrawn from the tissue. Jaws 161 may be opened to release the tissue. Leading edge 113 may be used with an RF energy source to coagulate the tissue to reduce bleeding. Core tube 110 contains the sample, which may be detached from the tissue with cutting, RF energy, and/or pulling. Capture tube 120 may be pulled back to open capture arms 130 and allow the sample to be removed from core tube 110.

Figure 5A:
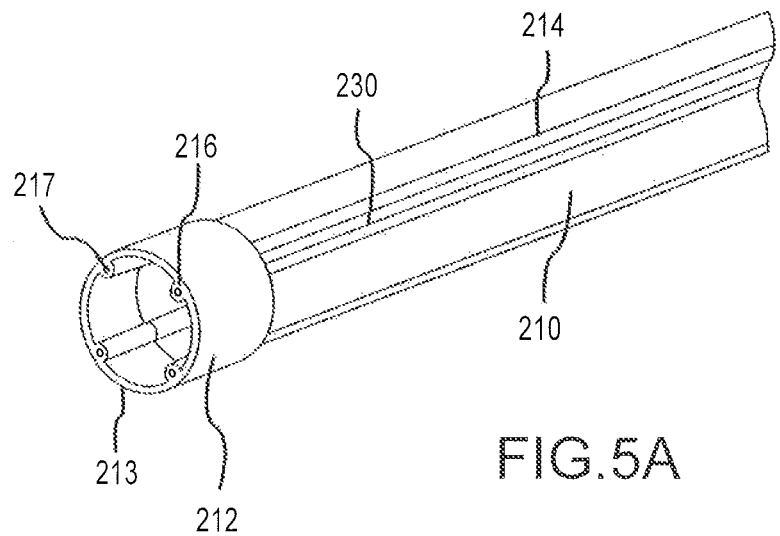
FIGS. 5A-5B show one embodiment of a biopsy device 200.
Figure 5B:
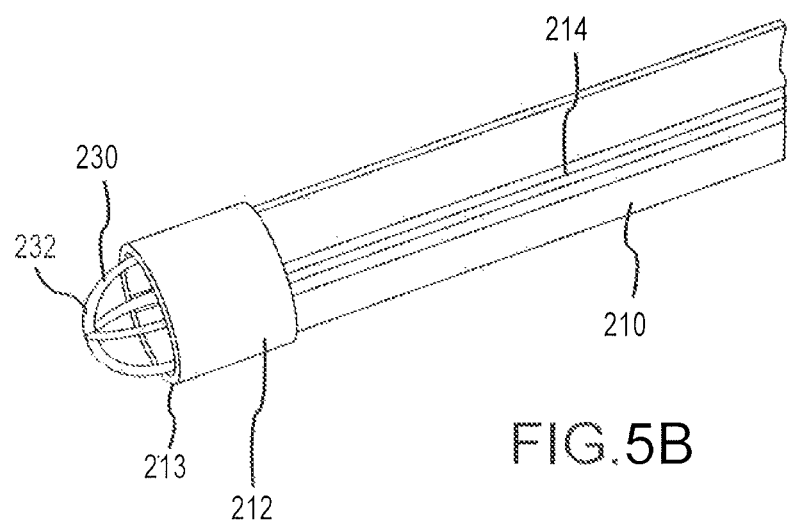

FIGS. 5A-5B show one embodiment of a biopsy device 200. FIG. 5A shows biopsy device 200 in an open position. FIG. 5B shows biopsy device 200 in a closed position.

Biopsy device 200 includes a core tube 210 and capture needles 230.

Core tube 210 includes a distal end 212 with a leading edge 213 configured to cut tissue. Distal end 212 may be reinforced with thicker tubing. Leading edge 213 is configured to work with an RF or other energy source for cutting tissue. Leading edge 213 may be blunt or atraumatic. Alternatively, leading edge 213 may be sharp, serrated, or other suitable configuration.

One or more needle channels 214 are formed longitudinally in the wall of core tube 210. Each needle channel 214 terminates at distal end 216 which is proximal to leading edge 213. An advancement hole 217 is formed in distal end 216 of each needle channel 214.

Needle channels 214 may be configured so that they do not protrude from the exterior of core tube 210. This allows core tube 210 to be more easily advanced into tissue. Alternatively, needle channels 214 may be configured so that they protrude from the exterior of core tube 210. This allows a greater volume of sample to be collected in core tube 210. Alternatively, core tube 210 may have a wall that is sufficiently thick such that needle channels 214 are formed completely within the wall of core tube 210, and do not protrude from the interior or exterior of core tube 210.

A capture needle 230 is slidably positioned in each needle channel 214. Capture needles 230 may be sharp, blunt, hooked, or other suitable configuration. Distal portions 232 of needles 230 may be coupled to an RF or other energy source to aid in penetrating tissue. Needle channels 214 may be open, closed, or otherwise configured to retain capture needles 230 in needle channels 214. Advancement holes 217 are configured to deflect distal portions 232 of capture needles 230 inward toward the center of core tube 210 when capture needles 230 are advanced. Advancement holes 217 may be angled, curved, and/or tapered to direct capture needles 230 toward the center of core tube 210.

FIGS. 6A-6D show one method of using biopsy device 200. Biopsy device 200 may be introduced through a previously placed sheath or cannula to reach the target tissue.

Figure 6A:
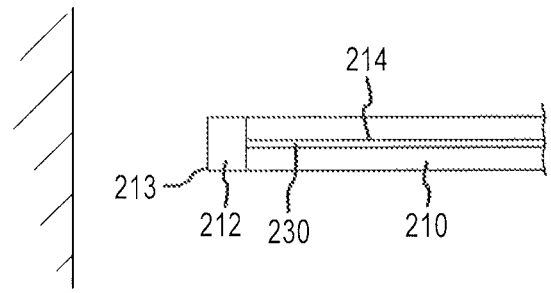
FIGS. 6A-6D show one method of using biopsy device 200.
Figure 6A:
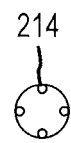

FIG. 6A shows biopsy device 200 in a cutting configuration. Capture needles 230 are retracted in needle channels 214.

Figure 6B:
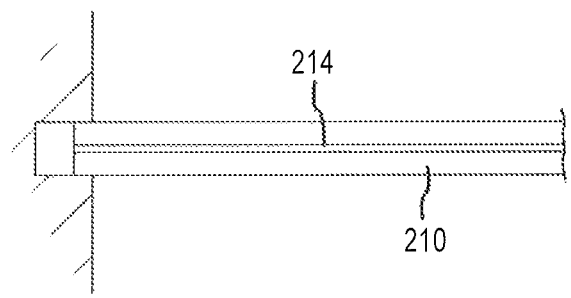
Figure 6B:
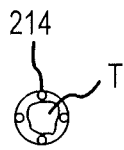

FIG. 6B shows biopsy device 200 advanced into a tissue. Core tube 210 is advanced into the tissue by using leading edge 213 and an RF energy source to cut into the tissue to a desired depth. The use of an RF energy source reduces bleeding.

Figure 6C:
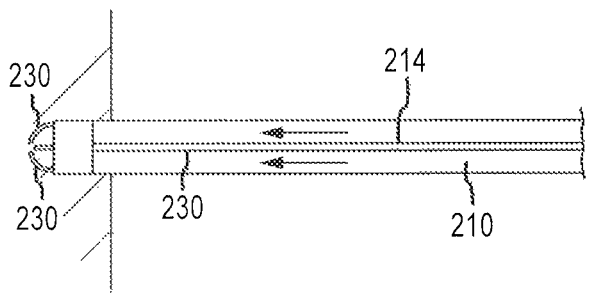
Figure 6C:
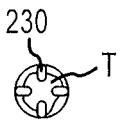

FIG. 6C shows biopsy device 200 in a capture configuration. Capture needles 230 are advanced in needle channels 214. Distal portions 232 of capture needles 230 are deflected by advancement holes 217 inward toward the center of core tube 210 and into the tissue. Distal portions 232 of capture needles 230 may be coupled to an RF energy source to aid in penetrating the tissue T.

Figure 6D:
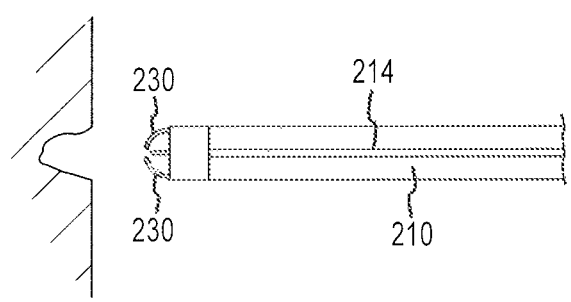
Figure 6D:

FIG. 6D shows biopsy device 200 withdrawn from the tissue. Leading edge 213 may be used with an RF energy source to coagulate the tissue to reduce bleeding. Core tube 210 contains the sample, which may be detached from the tissue with cutting, RF energy, and/or pulling. Capture needles 230 may be pulled back to allow the sample to be removed from core tube 210.

Figure 7A:
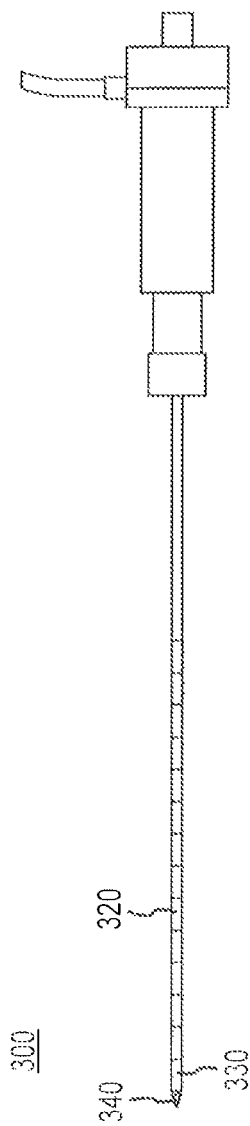
Figure 7C:
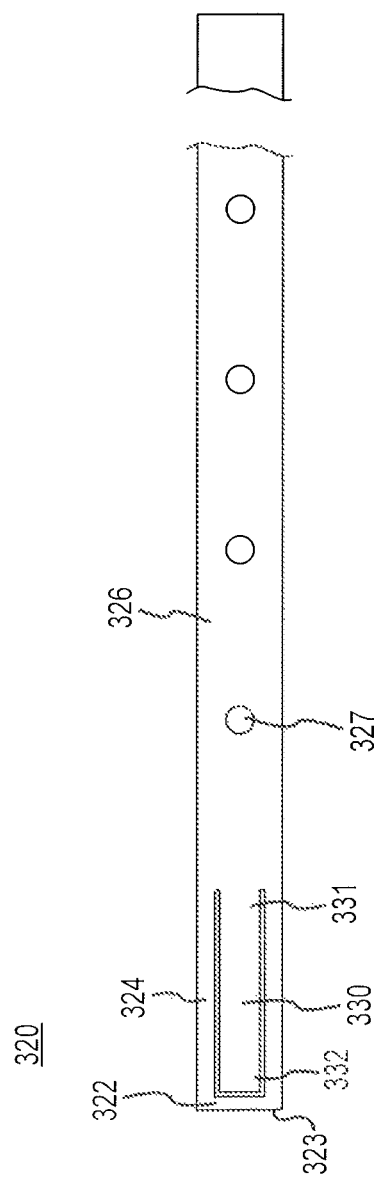
Figure 7D:
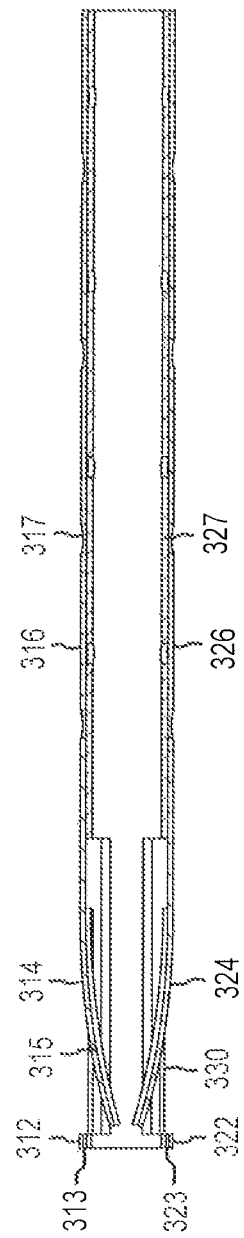

FIGS. 7A-7B show yet another embodiment of a biopsy device 300. FIG. 7A shows an overall view of biopsy device 300. FIG. 7B shows a core tube 310 of biopsy device 300. FIG. 7C shows a capture tube 320 of biopsy device 300. FIG. 7D shows a cross-sectional view of biopsy device 300.

Biopsy device 300 includes a core tube 310 and a capture tube 320 with capture arms 330.

Core tube 310 includes a leading section 312, a slotted section 314, and a cooling section 316.

Leading section 312 includes a leading edge 313 configured to cut tissue. Leading edge 313 is configured to work with an RF or other energy source for cutting tissue. Leading edge 313 may be blunt or atraumatic. Alternatively, leading edge 313 may be sharp, serrated, or other suitable configuration.

Slotted section 314 is proximal to leading section 312. Slotted section 314 includes one or more slots 315 formed longitudinally in the wall of core tube 310.

Cooling section 316 is proximal to slotted section 314. Cooling section 316 includes a plurality of cooling holes 317 formed in the wall of core tube 310.

Capture tube 320 is positioned concentrically around core tube 310. Capture tube 320 has an inside diameter that is greater than an outside diameter of core tube 310. Capture tube 320 can slide and rotate outside core tube 310. Capture tube 320 includes a distal section 322, a capture section 324, and a cooling section 326.

Distal section 322 may include a leading edge 323 configured to cut tissue in an alternative embodiment.

Capture section 324 is proximal to distal section 322. Capture section 324 includes one or more capture arms 330 formed longitudinally in the wall of capture tube 320. Capture arms 330 are biased inward toward the center of capture tube 320. Capture arms 330 are prevented from moving inward when not aligned with slots 315 of core tube 310. Capture arms 330 are allowed to move inward when aligned with slots 315. Core tube 310 may be rotated, advanced, and/or pulled back with respect to capture tube 320 to align slots 315 with capture arms 330. Each capture arm 330 may have a proximal end 331 that is attached to capture tube 320 and may have a distal end 332 that is free. Capture arms 330 may be blunt and coupled to an RF or other energy source to aid in cutting tissue. Alternatively, capture arms 330 may be sharp. Capture arms 330 may have features such as barbs, hooks, or other surface or material modifications to aid in grasping tissue. Capture arms 330 may be substantially rectangular or other suitable shape.

Cooling section 326 is proximal to capture section 324. Cooling section 326 includes a plurality of cooling holes 327 formed in the wall of capture tube 320. Cooling holes 327 of cooling section 326 of capture tube 320 are configured so that they may be aligned with cooling holes 317 of cooling section 316 of core tube 310.

Core tube 310 and capture tube 320 have inner surfaces and outer surfaces that are nonconductive. Core tube 310 and capture tube 320 may be made of a conductive material and insulated with an applied coating or bonded layer. For example, core tube 310 and capture tube 320 may have made of stainless steel or NITINOL™, and then core tube 310 and capture tube 320 may be made of stainless steel or NITINOL™, and then coated with PARYLENE™ by chemical vapor deposition. Cooling holes 317 and 327 may be sized and positioned to ensure complete coating of the interior surfaces or core tube 310 and capture 320. Other coatings used may be ceramic, polyimide, hybrids, ceramic nitrides, or any other suitable coating. Different coatings may be layered. Elements which are configured to transmit RF or other energy, such as leading edge 313, are not insulated and remain conductive. The insulation of core tube 310 and capture tube 320 ensure a sufficiently high current density at leading edge 313 to cut and coagulate. In addition, the insulation of the inside surface of core tube 310 reduces or prevents heat damage to the tissue sample. Alternatively, core tube 310 and capture tube 320 may be made of a nonconductive material, with leading edge 313 made of conductive material and coupled to an RF or other energy source with leads.

The following dimensions, equipment, and settings are given as an example for one specific embodiment of biopsy device 300, and are not meant to be limiting. Core tube 310 and capture tube 310 may have an overall length of approximately 10 in, and obtain core samples with lengths of approximately 0.5-1.0 in. Core tube 310 and capture tube 310 may have a diameter of approximately 0.125 in or less, with core tube 310 having an inside diameter of approximately 0.095 in or less. Core tube 310 and capture tube 310 may have a wall thickness of approximately 0.005 in. Capture arms 330 may have a length of approximately 0.25-0.75 in, and a width of 0.05-0.08 in. In one embodiment, capture arms have a length of approximately 0.306 in, and a width of approximately 0.06 in. The RF energy source may be an Aaron 125™ electrosurgical generator (Bovie Medical Corporation, Clearwater, Fla.), set to coagulation waveform and a power setting of 30. The RF energy source may also be a Force FX™ electrosurgical generator (Valleylab, Boulder, Colo.), set to coagulation waveform, monopolar operation, and a power setting of 30 to 60.

Stylet 340 is positioned within core tube 310. Stylet 340 has a distal end 342 that is sharp and pointed to puncture the skin or other surface to access a target tissue. Stylet 340 is configured to create a small puncture to reduce injury and healing time. Stylet 340 may be nonconductive. Stylet 340 may be made of a nonconductive material. Alternatively, stylet 340 may be made of a conductive material and then insulated. Stylet 340 may also be used with biopsy devices 100A, 100B, and 200.

FIGS. 8A-8F show one method of using biopsy device 300. Biopsy device 300 may be introduced through a previously placed sheath or cannula to reach the target tissue.

Figure 8A:
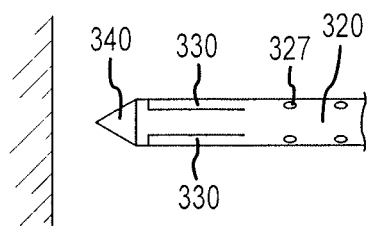
FIGS. 8A-8F show one method of using biopsy device 300.

FIG. 8A shows biopsy device 300 in an access configuration. Stylet 340 is positioned within core tube 310 and locked in place. Slots 315 are not aligned with capture arms 330, and core tube 310 holds open capture arms 330. Cooling holes 317 and 327 are aligned with each other.

Figure 8B:
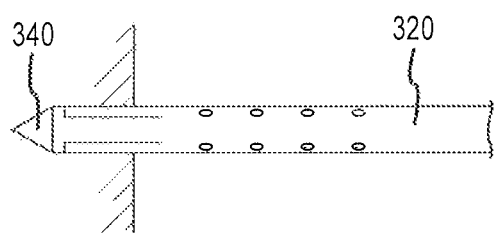

FIG. 8B shows biopsy device 300 advanced into a tissue. Stylet 340 is used to puncture a surface of the tissue and penetrate the tissue to allow leading edge 313 of core tube 310 to be positioned at a desired depth.

Figure 8C:
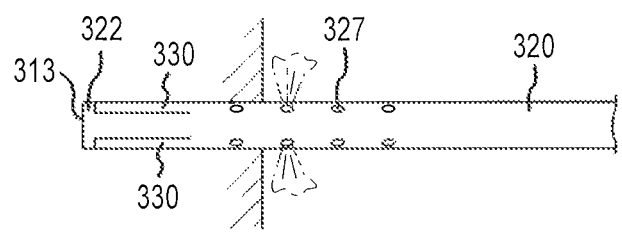

FIG. 8C shows biopsy device 300 in a cutting configuration. Stylet 340 is withdrawn through core tube 310. Core tube 310 is further advanced into the tissue by using leading edge 313 and an RF energy source to cut into the tissue to obtain the tissue sample. The use of an RF energy source reduces bleeding. Heat and steam may escape through cooling holes 317 and 327. In addition, heat and steam escaping through cooling holes 317 and 327 may generate a vacuum which aids in drawing tissue into core tube 310.

Figure 8D:
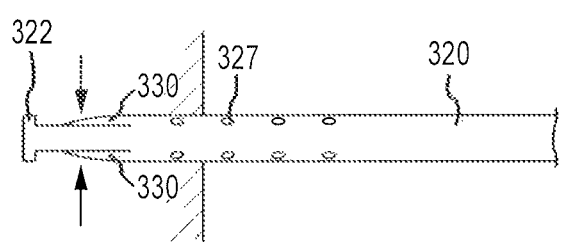

FIG. 8D shows biopsy device 300 in a capture configuration. Core tube 310 and capture tube 320 are rotated, advanced, and/or pulled back with respect to each other to align slots 315 with capture arms 330. Capture arms 330 are thus allowed to close inward through slots 315 and grasp the sample inside core tube 310. Each capture arm 330 may have a distal end 332 which is coupled to an RF energy source to aid in cutting the tissue.

Figure 8E:
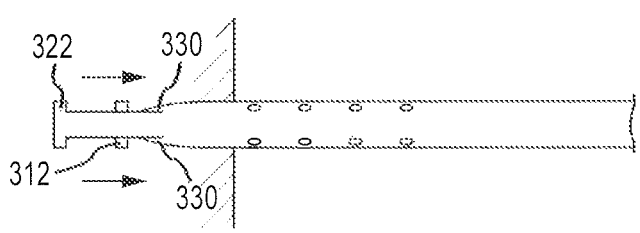

FIG. 8E shows biopsy device 300 in an optional cinching configuration. Core tube 310 may be pulled back with respect to capture tube 320. Leading section 312 of core tube 310 is pulled back so that leading section 312 encircles capture arms 330. Capture arms 330 are thus cinched together and grasp more tightly the sample inside core tube 310.

Figure 8F:
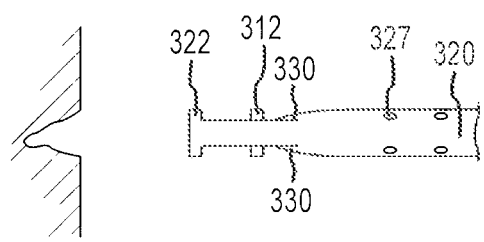

FIG. 8F shows biopsy device 300 withdrawn from the tissue. Leading edge 313 may be used with an RF energy source to coagulate the tissue to reduce bleeding. Core tube 310 contains the sample, which may be detached from the tissue using cutting, RF energy, and/or pulling. Capture tube 320 may be pulled back to open capture arms 330 and allow the sample to be removed from core tube 310.

Figure 9A:
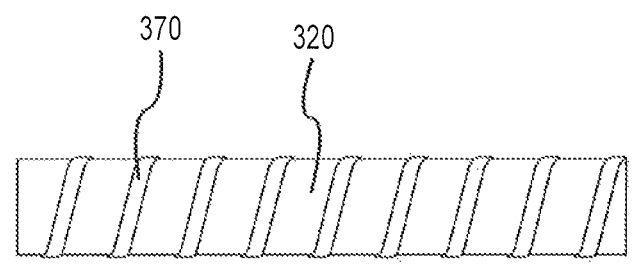
FIGS. 9A-9B show one embodiment of a coagulation electrode 370.
Figure 9B:
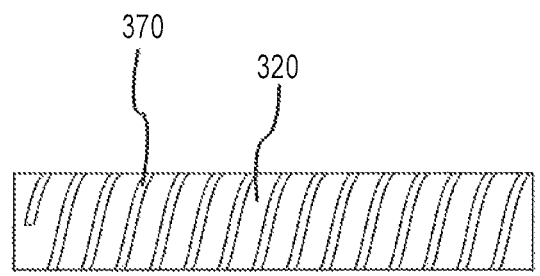

FIGS. 9A-9B show one embodiment of a coagulation electrode 370. FIG. 9A shows coagulation electrode 370 in a monopolar configuration. FIG. 9B shows coagulation electrode 370 in a bipolar configuration.

Coagulation electrode 370 may be used to reduce bleeding when tissue is being cut. Coagulation electrode 370 may be a conductive ink painted or applied on an outside surface of capture tube 320. Alternatively, coagulation electrode 370 may be a wire embedded or otherwise coupled to an outside surface of capture tube 320.

Coagulation electrode 370 may have a helical or double helical configuration, for monopolar or bipolar configurations, respectively. Coagulation electrode 370 may be limited to a portion of capture tube 320 that is advanced into tissue. Coagulation electrode 370 may also be used with capture tube 120, core tube 210, and other elements.

The biopsy devices described herein may be used to obtain samples from a lung while reducing the size of the wound created at the biopsy site. The biopsy devices are used with RF or other energy, which reduces bleeding at the biopsy site. The combination of the small wound size and the use of RF or other energy may facilitate the sealing of the wound at biopsy site when the biopsy device is withdrawn and eliminate the need for a chest tube to prevent pneumothorax. The biopsy devices described herein may also be used to obtain samples from a kidney, liver, or other internal organ.

While the foregoing has been with reference to particular embodiments of the invention, it will be appreciated by those skilled in the art that changes in these embodiments may be made without departing from the principles and spirit of the invention.

All publications and patent applications mentioned in this specification are herein incorporated by reference to the same extent as if each individual publication or patent application was specifically and individually indicated to be incorporated by reference.

What is claimed is:

1. A biopsy device for obtaining a biopsy sample from a tissue, the biopsy device comprising:
    a core tube including
        a leading section including a leading edge,
        a slotted section proximal to the leading section, the slotted section including a longitudinal slot defined by a wall of the core tube, and
        a core tube cooling section proximal to the slotted section, the core tube cooling section including a plurality of core tube cooling holes defined by the wall of the core tube; and
    a capture tube slidably and rotatably coupled concentrically around the core tube, the capture tube including
        a distal section,
        a capture section proximal to the distal section, the capture section including a longitudinal capture arm defined by a wall of the capture tube, the capture arm being biased inward, wherein the capture arm cannot move inward when not aligned with the slot in the core tube, and wherein the capture arm can move inward when aligned with the slot in the core tube, and
        a capture tube cooling section proximal to the capture section, the capture tube cooling section including a plurality of capture tube cooling holes defined by in the wall of the capture tube, wherein the core tube cooling holes are capable of being aligned with the capture tube cooling holes.

2. The biopsy device of claim 1, wherein the leading edge is blunt.

3. The biopsy device of claim 1, wherein the leading edge is coupled to an RF energy source.

4. The biopsy device of claim 1, wherein the leading edge is conductive, and wherein the core tube and the capture tube other than said leading edge are not conductive.

5. The biopsy device of claim 1, wherein the core tube and the capture tube are made of a conductive material, and wherein inner surfaces and outer surfaces of the core tube and the capture tube are coated with an insulating coating.

6. The biopsy device of claim 1, wherein leading edge is made of a conductive material, and wherein the core tube and the capture tube other than said leading edge are made of a nonconductive material.

7. The biopsy device of claim 1, wherein the leading edge is cylindrical.

8. The biopsy device of claim 1, wherein the capture arm is rectangular.

9. A method, including steps of
    providing a biopsy device including a core tube including a slot and a capture tube including a capture arm;
    advancing the core tube into the tissue by using a leading edge on a distal end of the cors tube and partially filling the core tube with the tissue;
    grasping the tissue with the capture arm by aligning the slot with the capture arm to allow the capture arm to move inward;
    removing the sample by withdrawing the core tube and the capture tube; and
    allowing heat and steam to escape through a plurality of cooling holes formed in the core tube and capture tube.

10. The method of claim 9, wherein advancing the core tube into the tissue includes using an RF energy source coupled to the leading edge to aid in cutting the tissue.

* * * * *